United States Patent [19]

Rogers et al.

[11] 4,172,450
[45] Oct. 30, 1979

[54] METHOD AND APPARATUS FOR DETERMINING THE INSTANTANEOUS ARTERIAL BLOOD PRESSURE

[75] Inventors: Thomas Rogers, Glasgow, Scotland; Colin G. Caro, Richmond, England

[73] Assignee: Barr & Stroud Limited, Glasgow, Great Britain

[21] Appl. No.: 800,230

[22] Filed: May 25, 1977

[30] Foreign Application Priority Data

May 26, 1976 [GB] United Kingdom ............... 21753/76

[51] Int. Cl.² ............................................. A61B 5/02
[52] U.S. Cl. ................................................ 128/679
[58] Field of Search ............. 128/2.05 A, 2.05 G, 128/2.05 M, 2.05 P, 2.05 Q, 2.05 R

[56] References Cited

U.S. PATENT DOCUMENTS

| | | | |
|---|---|---|---|
| 3,156,237 | 11/1964 | Edmark, Jr. ..................... | 128/2.05 R |
| 3,157,177 | 11/1964 | Smith ............................... | 128/2.05 A |
| 3,527,197 | 9/1970 | Ware ................................ | 128/2.05 A |
| 3,572,320 | 3/1971 | Gerold et al. .................... | 128/2.05 G |
| 3,769,964 | 11/1973 | Smith ............................... | 128/2.05 G |

*Primary Examiner*—William E. Kamm
*Attorney, Agent, or Firm*—Mason, Fenwick & Lawrence

[57] ABSTRACT

A method of determining the instantaneous arterial blood pressure of a subject which is a living being without utilizing entry of a needle or the like along an artery is capable of a high degree of accuracy and comprises the steps of applying a pressurizable device in the region of an artery and controllably pressurizing that device with fluid to an extent sufficient to eliminate arterial wall movement without collapse of the artery, the fluid pressure in the pressurizable device being monitored and providing a measure of the instantaneous arterial blood pressure of the subject. A preferred form of pressurizable device is an annular ring or cuff comprising a rigid body of annular shape over the inner surface of which is stretched a latex membrane which is pressurizable with distilled water.

6 Claims, 7 Drawing Figures

METHOD AND APPARATUS FOR DETERMINING THE INSTANTANEOUS ARTERIAL BLOOD PRESSURE

This invention relates to a method of and apparatus for determining the instantaneous arterial blood pressure of a subject which is a living being such as a human or any other animal, and for determining various biological parameters of that subject.

The arterial blood pressure of a subject requires to be determined and monitored or analysed for a variety of medical reasons. Hitherto, such determination has either been by an invasive technique requiring entry of a transducer or a catheter or needle attached to a transducer along an artery or by a non-invasive technique using a pressurisable cuff wrapped around a limb (usually the arm in the case of a human subject) or a sphygmomanometer and stethoscope. The invasive technique requires clinically sterile conditions and is potentially dangerous to the subject but is capable of providing sufficient information to enable the instantaneous blood pressure and the waveform thereof to be determined with accuracy. The known non-invasive technique does not require any special clinical conditions and is harmless to the subject but is not capable of providing sufficient accurate information to derive the true instantaneous arterial blood pressure.

It is an object of the present invention to provide a method of and apparatus for accurately determining instantaneous arterial blood pressure by a non-invasive technique and which obviates or mitigates the above-mentioned disadvantages.

It is a further object to provide apparatus for determining various biological parameters of a subject.

According to the present invention there is provided a method of determining the instantaneous arterial blood pressure of a subject which is a living being comprising the steps of applying a pressurisable device in the region of an artery and controllably pressurising said device with fluid sufficiently to eliminate arterial wall movement other than by collapsing the artery, and monitoring the fluid pressure in the pressurisable device, the monitored fluid pressure being a measure of the instantaneous arterial blood pressure of the subject.

Preferably said fluid is heated to a temperature which is compatible with the blood temperature of the subject. Conveniently, the fluid is at a temperature within the range 20°–38° C.

Further, according to the present invention there is provided a method of determining the instantaneous arterial blood pressure of a subject which is a living being, comprising the steps of locating adjacent an artery of the subject, a first sensor device which is pressurisable with fluid, pressurising the first sensor device with fluid from a controllable source, and monitoring the output of said first sensor device, initially adjusting the mean fluid pressure applied to the first sensor device to a first level to permit monitoring of fluid pressure fluctuations in the first sensor device resulting from arterial blood pressure, locating a second sensor device adjacent an artery of the subject, deriving a control signal from the output of said second sensor device, applying said control signal to said controllable source having caused the absence of a monitored signal in the first sensor device resulting from arterial blood pressure, adjusting the amplitude of said control signal to enable the resultant monitored fluid pressure fluctuations in the first sensor device to be substantially identical in amplitude to those initially monitored at the output of the first sensor device due to arterial blood pressure, whereby in the presence of arterial blood pressure in the artery and in the presence of said amplitude-adjusted control signal and at said first level of mean fluid pressure arterial wall movement due to instantaneous pressure of blood in the artery is substantially eliminated adjacent the first sensor device, and the monitored fluid pressure in the first sensor device is a measure of the instantaneous arterial blood pressure.

Preferably, said first level of means fluid pressure enables monitoring at maximum amplitude of said fluid pressure fluctuations resulting from arterial blood pressure.

When the first sensor device is in the form of a pressurisable cuff the amplitude adjustment of the control signal may be undertaken either when the artery is obstructed upstream, e.g., by use of a tourniquet, or when the standing fluid pressure in the cuff is in excess of the systolic pressure of the subject's arterial blood pressure.

The control signal may be derived directly from the subject by means of a sensor device in the form of a transducer such as an ear densitometer or, preferably, a further cuff wrapped around the same or another limb, preferably a corresponding limb, of the subject. In the case where the control signal is derived from an ear densitometer the output of the densitometer is first processed to match the output of the pressurisable sensor device in the shape and in amplitude when the mean fluid pressure applied to the pressurisable sensor device is at said first level.

Further according to the present invention there is provided apparatus capable of carrying out the method of the fourth preceding paragraph and for determining biological parameters of the subject, comprising a pressurisable sensor device adapted to be located in the region of a subject's artery, a controllable source of fluid coupled to said device, means for monitoring the fluid pressure in the device, and means for applying a control signal to said source of fluid.

The controllable source of fluid may comprise a pump having an adjustable stroke and the control-signal-applying means may comprise a servo system which drives the pump.

The pressurisable device may be in the form of a cuff comprising a resiliently flexible bag shrouded by a substantially rigid barrier so that, in use, the bag is interposed between the subject's limb and the barrier. Alternatively, the cuff may incorporate one or more pressurisable pads mounted within a rigid barrier.

Embodiments of the present invention will now be described by way of example with reference to the accompanying drawings in which.

Figure 1:
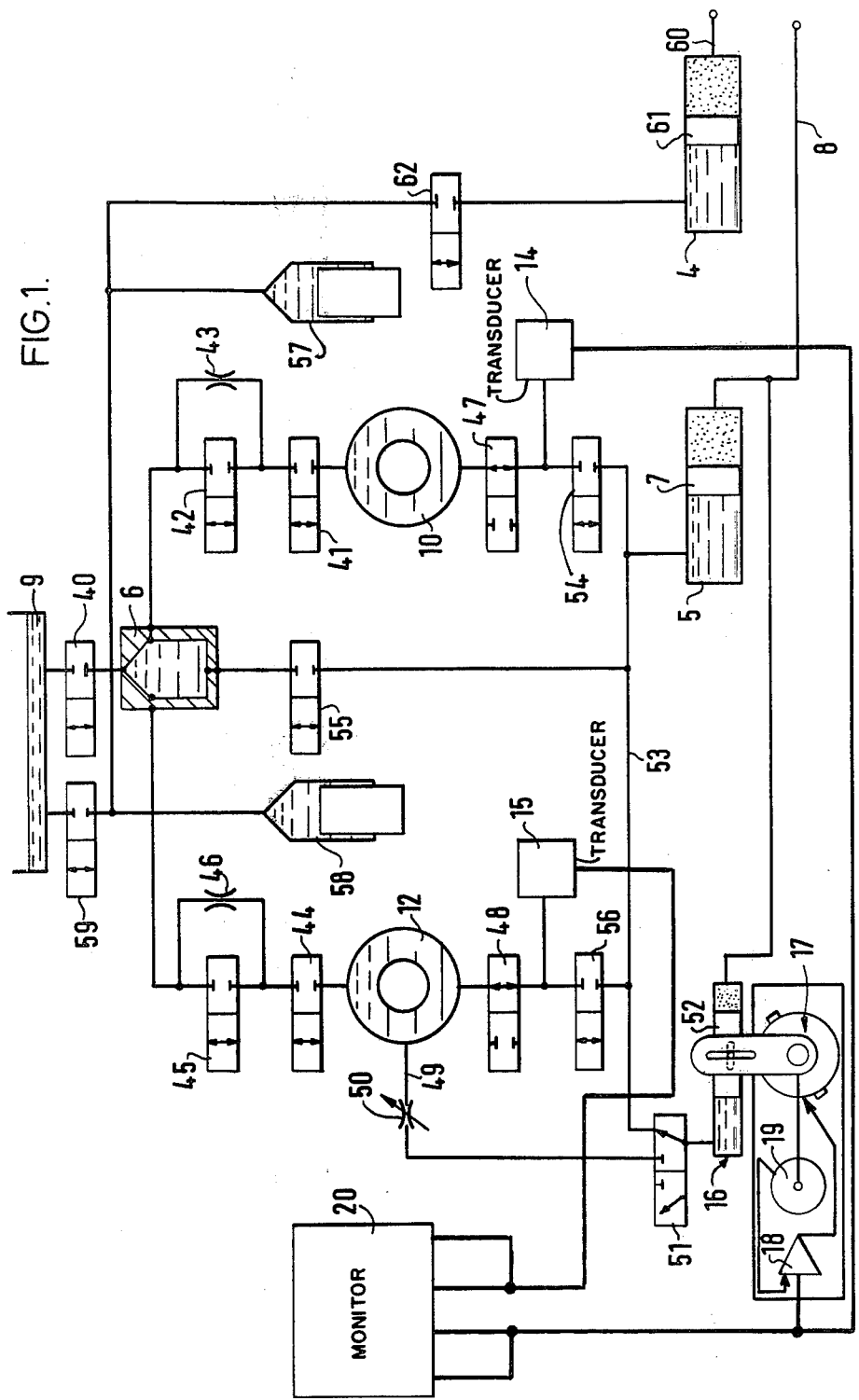
FIG. 1 is a block diagram of apparatus according to the present invention.

The embodiment shown in FIG. 1 is for use with a human subject and comprises a first or distal pressurisable sensor device, in the form of a cuff 12 which is located around the index finger of the subject's left hand. A similar pressurisable sensor device in the form of a cuff 10, referred to as the proximal cuff, is located around the index finger of the subject's right hand. The cuffs are referred to as distal and proximal (with respect to the blood flow path from the heart) to identify the functions of the two cuffs when they are both located on the same limb as will be explained.

Figure 3:
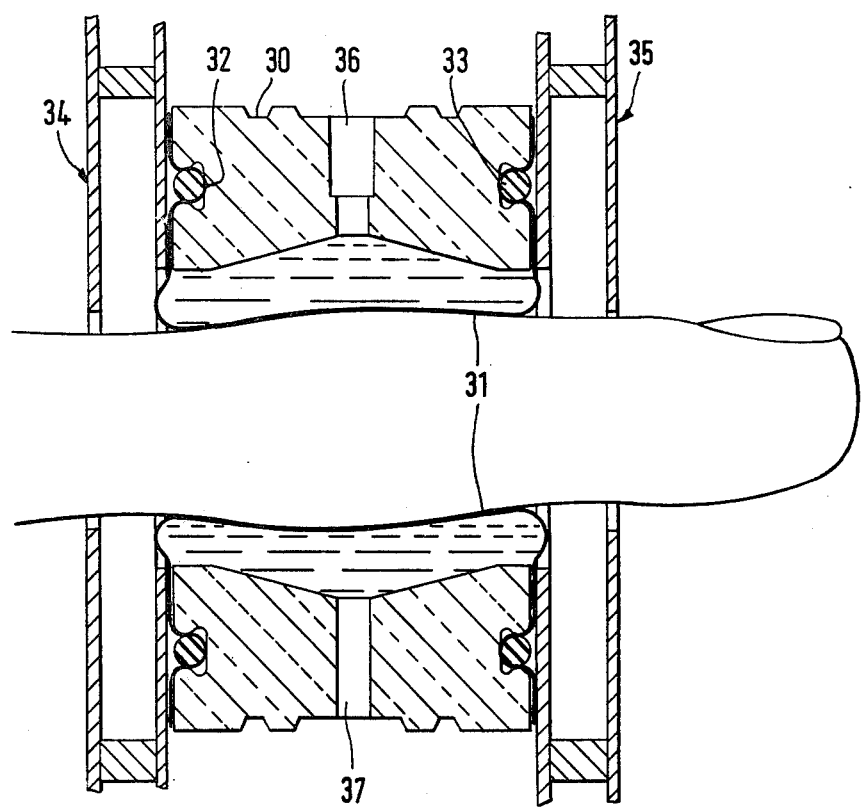
FIG. 3 is an explanatory drawing of a detail of FIG. 1.

Each cuff is preferably as illustrated in FIG. 3 and comprises an annular rigid body 30 made of clear plastics material, a thin-walled flexible and resilient bag 31 formed by a rubber or latex membrane secured to the body 30 by O-rings 32, 33 and end clamps 34, 35 each being adjustable in aperture whereby when the finger of a subject is fitted to a cuff the clamps 34, 35 can be adjusted in aperture to match the size of the finger thereby causing the bag 31 to be constrained only by rigid bodies and by the subject's finger. The rigid body 30 includes an inlet 36 for receiving pressurising fluid for the bag 31 and an orifice 37 for connection of a pressure transducer.

The bags 31 of the cuffs 10, 12 are filled with liquid (e.g., distilled water) from a low impedance fluid source in the form of a cylinder 5, with an associated header tank 9, and are pressurised by a pneumatic line 8, the pneumatic and liquid components being separated by a precision ground piston 7 slidable in the cylinder 5. The header tank 9 is connected through an ON/OFF valve 40 to a heater chamber 6 which is arranged to heat the liquid being supplied to the bags 31 of the cuffs 10, 12 to a temperature which is compatible with the blood temperature of the subject. For example 20°–38° C. The chamber 6 is connected to the bag 31 of the cuff 10 through an ON/OFF valve 41 connected in series with the parallel connection of an ON/OFF valve 42 and a throttle device 43. The cuff 12 is likewise connected through an ON/OFF valve 44 in series with an ON/OFF valve 45 in parallel with a throttle 46. Thus either a full flow of fluid can be provided to fill the bags 31 of the cuffs 10, 12 or a throttled or restricted flow can be made available for operational use as will be explained. Transducers 14, 15 are connected to the bags 31 of the cuffs 10, 12 respectively in order to monitor the fluid pressure therein, being connected through ON/OFF valves 47, 48 respectively.

The bag 31 of the cuff 12, in addition to being connected to the fluid source formed by cylinder 5, is connected by way of a conduit 49 to a pump 16 which acts as a high impedance controllable source of pressurised fluid. The conduit 49 includes a throttle 50 and a valve 51.

The pump 16 is of adjustable stroke and is driven by a servo system incorporating a motor 17 which is energised by a servo amplifier 18 connected electrically to the output of the transducer 14. A position-feedback-potentiometer 19 is coupled to the motor 17 and applies a feedback signal to the amplifier 18. The motor 17 drives a piston 52 contained in a cylinder which is connected to the pneumatic line 8. The valve 51, in addition to being connected to the conduit 49 is connected to one end of a conduit 53. The conduit 53 connects to low-impedance pressurising cylinder 5 and through any one of ON/OFF valves 54, 55, 56 to the transducer 14, the heater chamber 6 and the transducer 15 respectively. Because of the various flow-restrictions in the hydraulic conduits the standing or mean pressure in the bags 31 of the cuffs 10, 12 is equal but the cuffs can be isolated from each other in relation to transient changes in pressures.

In order to operate the clamps 34, 35 of each of the cuffs 10, 12 hydraulic actuators 57, 58 are provided, being supplied with hydraulic fluid from a cylinder 4 by way of an ON/OFF valve 62 and being pressurised pneumatically by means of an air supply 60 acting on a free piston 61 contained in the cylinder 4 the hydraulic line to which contains an ON/OFF valve 62.

Electrically connected to the outputs of the transducers 14, 15 is a a monitoring apparatus 20. The apparatus 20 has four channels for monitoring the instantaneous and the mean pressure levels in each of the cuffs 10, 12.

Figure 2:
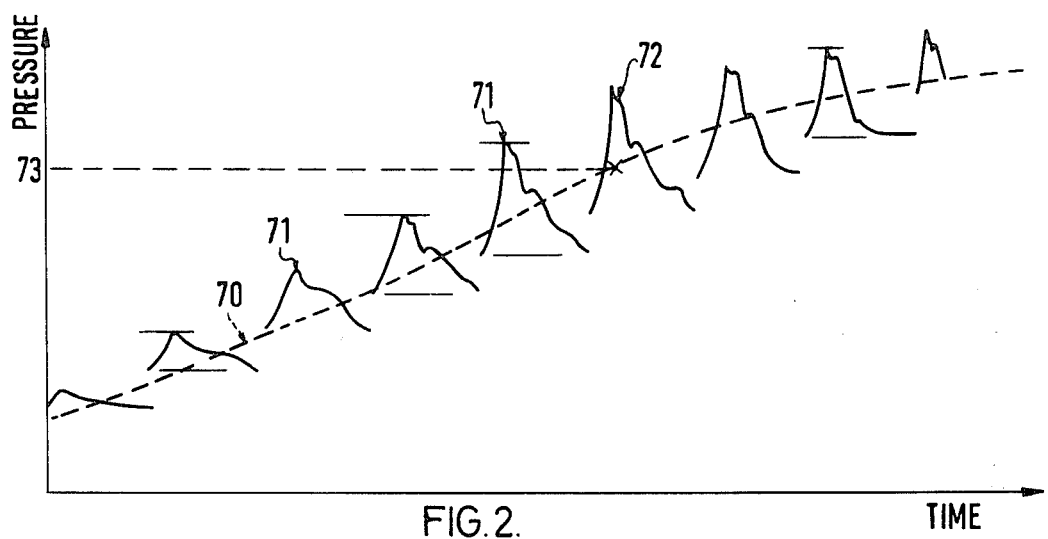
FIG. 2 illustrates typical waveforms which occur in the apparatus of FIG. 1.

When the embodiment of FIG. 1 is rendered operational by being connected to a patient the servo amplifier 18 is initially disabled and the level of standing or mean pressure applied to the hydraulic fluid in each of the cuff bags is adjusted to permit monitoring of the fluctuating fluid pressure signal due to instantaneous arterial blood pressure. This is achieved by placing valves 41, 44, 55 in the OPEN position and adjusting the pneumatic pressure in line 8. The waveform which is monitored by apparatus 20 for each of the cuffs is of the form shown in FIG. 2 wherein line 70 denotes the mean or standing pressure applied and the fluctuating signal due to instantaneous blood pressure is denoted 71. It will be noted that as the mean pressure increases from its lowest value the peak-to-peak value of the signal 71 increases, reaches a maximum, then decreases. The maximum peak-to-peak value is denoted 72 and the value of mean pressure at which this occurs 73. This level of mean pressure is referred to hereinafter as the "first level."

The mean hydraulic pressure is maintained at said first level by the regulated air pressure in line 8, and thereafter the artery supplying the finger in cuff 12 is obstructed, for example by applying a conventional tourniquet to the arm of the subject on the upstream side of the cuff 12. The amplifier 18 is enabled and the valve 51 is changed over in position then the gain of the amplifier 18 is adjusted until such time as the transient or fluctuating waveform monitored by the apparatus 20 at the output of transducer 15 is substantially identical in amplitude to the previously recorded waveform 72.

The tourniquet restriction is removed from the subject and the signal thereafter monitored at the output of the transducer 15 is the desired measure of the instantaneous arterial blood pressure after transients have died down.

In order to achieve consistent results with the above described embodiment it is desirable to coat the index fingers of the subject with a lubricant which is compatible with the membrane material of the bags 31. For example if the bag 31 is made of latex, K.Y. Jelly is suitable as a lubricant. This facilitates slip of the membrane over the finger and by filling in hollows around the knuckle areas. Initially when liquid enters the bags 31 it requires to displace air between the bags and the fingers and to achieve this completely liquid may be injected repeatedly into the cuff bags and the hydraulic pressure raised to say 250 mm Hg. Any air contained within the cuff bag is collected within the heater chamber 6, then vented to atmosphere through valve 40. The cuff end clamps 34, 35 are tightened hydraulically to an extent which does not significantly throttle the arterial pulse and at the same time locates the membrane bag 31 by preventing the bag ballooning out when the hydraulic pressure is raised above systolic pressure.

Figure 4:
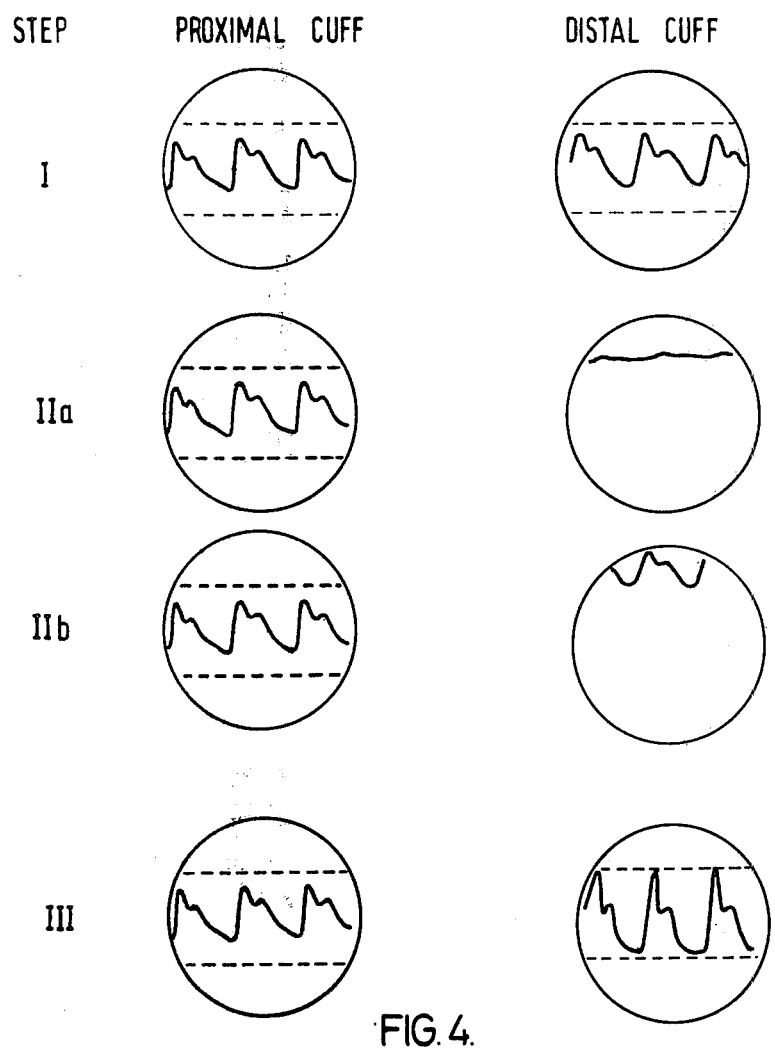
FIG. 4 shows various waveforms which occur in the apparatus of FIG. 1 when operated in accordance with the method of the present invention.

In FIG. 4 the waveforms appearing in the apparatus 20 are shown for the various sequential steps described above. In the step with the amplifier 18 disabled, denoted Step I, the monitored waveforms from the two cuffs are substantially identical but are distorted versions of the true or exact arterial blood pressure waveforms, the pressure excursion between systolic and diastolic is typically about 50% of the true arterial pressure excursions. In the step with an absence of a monitored waveform in the first cuff 12, denoted Step II, waveform (a) occurs when the standing pressure applied to the cuff 12 is in excess of the systolic pressure and waveform (b) occurs after enabling and adjusting the gain of the amplifier 18, the pressure excursion in this waveform being the same as that occuring in Step I. Step III illustrates the waveform finally produced by transducer 15, the mean or standing pressure being the same as that of the two waveforms of Step I, and this fluctuating waveform is substantially identical to the true arterial blood pressure waveform both in wave shape and in pressure excursion.

Figure 5:
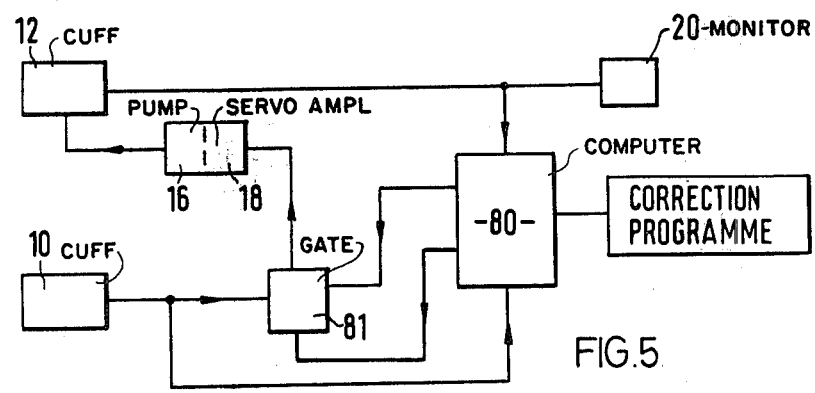
FIGS. 5 and 6 are block diagrams of modified apparatus according to the present invention.

It will now be appreciated from the foregoing discussion that the fluid pressure applied to the cuff 12 is modified by the application of a control signal which is correct in timing in relation to the instantaneous arterial blood pressure, this control signal being derived in the case of the described embodiment from a second cuff 10 applied to the subject. But the control signal may be derived from any one of several sources. For example, FIG. 5 illustrates an embodiment wherein the outputs of the two cuffs 10, 12 are compared in a computer 80 (either digital or analogue with input filter) which, under the guidance of a learning programme, outputs a control signal to the servo amplifier 18 via a controlled gate 81. As a result of iteration the recorded waveform in apparatus 20 will be substantially identical to the true arterial waveform.

Figure 6:
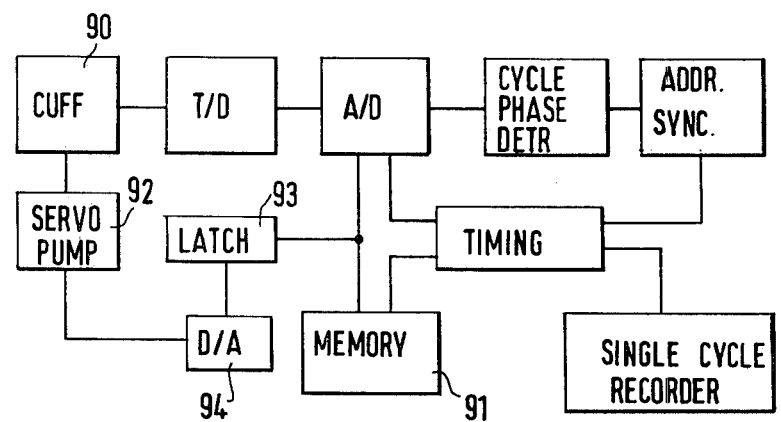

In another arrangement, illustrated in FIG. 6, only a single cuff 90 is used. To utilise this arrangement the mean pressure applied to the cuff 90 is adjusted to the level 73 (of FIG. 2) and one complete cycle of the resultant waveform 72 is recorded in a memory 91. Thereafter this recorded or memorised waveform in memory 91 is fed to a latch 93 and a D/A converter 94 to provide the control signal for the cuff 90 with the servo-pump system 92 in circuit. The gain setting of system 92 is preset at fraction of the setting required for the previous system. In this case it is necessary continuously to update the memory 91 from the enhanced signal emanating from the cuff 90 and to synchronise the control signal with the true waveform resulting from the arterial blood pressure and this is achieved by detecting the initiation of the waveforms ascent to systolic from diastolic and triggering a timing device. Additionally, it may become necessary to vary the time interval of the recorded cycle in the event that the subject has an arythmic heart operation. Thus the occurrence of the systolic peak in the recorded waveform can be timed to coincide with the actual systolic peak.

Although the cuffs, 10, 12 have been disclosed as applied to the fingers of a subject any artery-containing limb would suffice with cuffs of appropriate capacity. Each cuff is preferably in the form of a thin-walled flexible and resilient bag (e.g., made of a rubber-like material) shrouded by a substantially rigid backing as illustrated in FIG. 3 and in accordance with the foregoing disclosure the pressurising of the fluid (e.g., water) in the bag eliminates arterial wall movement due to arterial blood pressure variations and compensates for displacement of tissue along the limb by variation of the quantity of liquid in the cuff bag so that the total volume of liquid in the cuff bag and tissue between the artery and the rigid cuff backing remains constant.

The present invention is based upon the theory that $$P_i = P_m + (C_{st}/C_{art})(P_m - P_c) \qquad 1$$

Where
- $P_i$ = pressure in the artery
- $P_m$ = pressure of cuff 12 as measured by the cuff transducer 15 when the pump is under servo control;
- $P_c$ = pressure of cuff 10 as measured by cuff transducer 14 and representing the control signal;
- $C_{st}$ = compliance of soft tissue in the limb as measured with the FIG. 1 apparatus operational;
- $C_{art}$ = compliance of artery in the limb as measured with the FIG. 1 apparatus operational.

It can be shown from theoretical considerations that the above relationship exists to a first approximation and the better the approximation that $P_c = P_m$, the better is the approximation that $P_m = P_i$.

By way of example, relating to the figures given above, $P_c \approx 0.5 \, P_i$ and if the apparatus operates as described above $C_{art} \approx 10 \, C_{st}$ from which it follows that $P_m = 0.95 \, P_i$.

It will be appreciated that the apparatus of FIG. 1 provides a measurement of instantaneous arterial blood pressure at the location of a subject's finger. If the subject has been tested in a sitting position with the fingers at a different level from the upper arm a pressure correction can be applied to provide the pressure levels at the upper arm which is the conventional measuring point for human subjects. If the height difference between fingers on a desk and the upper arm is 136 mm this equates to a hydrostatic pressure difference of 10 mm Hg (density of Hg to that of blood is 13.6 to 1.) Thus the arterial pressure in the finger will be greater than the upper arm arterial pressure by about 10 mm Hg.

It will be further appreciated that although the apparatus of FIG. 1 utilises a pressurisable cuff which is wrapped around a limb a pressurisable pad could be used in the proximity of an artery at any location where the pad can co-operate with a relatively rigid member of the subject, such as a bone. Thus a pressurisable pad could be used on the subjects temple or behind the ear, but in each case is for the purpose of restraining volume changes in the artery concerned when the pad is operated by the servo system. Utilising this apparatus the instantaneous arterial blood pressure of a subject can be determined with a substantial degree of accuracy and utilising non-invasive techniques.

The apparatus described above can also be utilised for the measurement of various biological parameters a knowledge of which is valuable for example in assessing the action of drugs.

The apparatus of FIG. 1 can be used with the servo system operational to determine the apparatus compliance of the soft tissue at the site of the servo-controlled cuff 12. This is achieved by obstructing the artery supplying the area under the cuff 12 so that due to flattening the artery compliance $C_{art}$ becomes very small relative to the soft-tissue compliance $C_{st}$. The standing pressure applied to the cuff 12 is then adjusted to a pressure value of interest, e.g., diastolic or mean arterial blood pressure, and a preset volume change is induced in the fluid-filled bag of the cuff 12 by application of a calibrated electronic signal to the servo amplifier 18. The resulting pressure rise in the cuff 12 is monitored and the apparent soft-tissue compliance calculated from the relationship $$C_{st} = \frac{\text{Volume of fluid injected}}{\text{pressure change detected}}$$

i.e. $C_{st} = \frac{\Delta V}{\Delta P}$

Typically, the injected volume change is of the order of 0.1 ml and by successively increasing to this volume by 0.01 ml increments the apparent soft-tissue compliance can be measured over a range of pressures.

Figure 7:
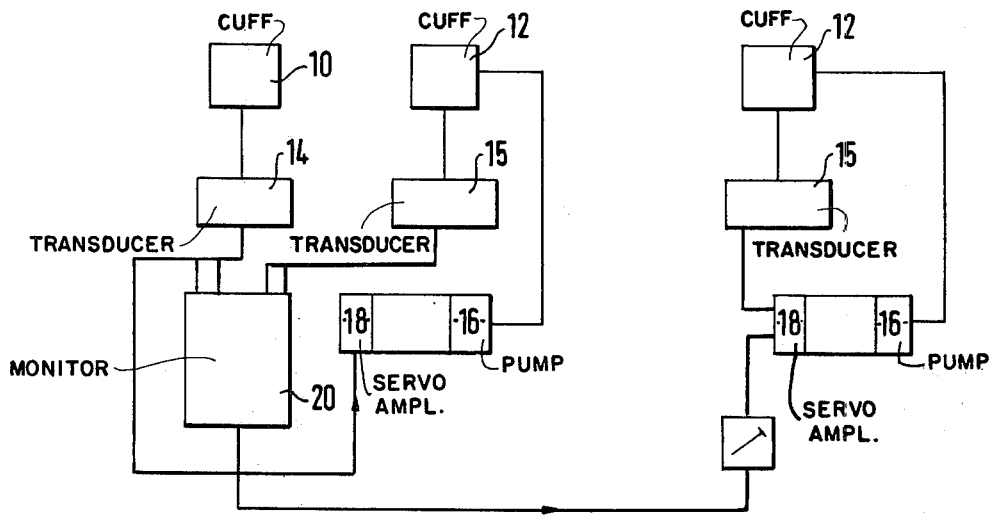
FIG. 7 shows a further modification of the apparatus according to the present invention.

The apparatus of FIG. 1 can be used in duplex as shown in FIG. 7 to determine the compliance of the artery by arranging one form of the apparatus to operate with the servo system operational to monitor the instantaneous arterial blood pressure from which the value of the pressure at a particular point in the pressure waveform can be determined (this may for example be the diastolic value). This specific pressure value is then set as the standing pressure in the cuff 12 of the other form of the apparatus and the servo system thereof is operated in a closed loop to maintain this pressure value in the cuff 12 despite the pressure and volume changes of the artery therein due to the normal arterial blood pressure fluctuations. The fluctuation in fluid volume of the servo-controlled pump of the apparatus 30 then provides a measure of the artery volume change over the transmural pressure range zero to peak pulse pressure.

The ratio ($\Delta V/\Delta P$) can be determined over this pressure excursion and represents the effective compliance of the artery in the presence of the soft tissue, i.e., $$\frac{1}{\Delta V/\Delta P} = \frac{1}{C_{st}} + \frac{1}{C_{st}}$$

and from this $C_{art}$ can be determined since $C_{st}$ can be determined as described above.

We claim:

1. A method of determining the instantaneous arterial blood pressure of a subject which is a living being, comprising the steps of:
   applying a servo-controlled fluid-pressurisable device to the subject in the region of an artery,
   deriving a control signal for the servo of said pressurisable device from the subject's blood pressure,
   calibrating the servo-controlled fluid pressurisable device with respect to the subject,
   and monitoring the fluid pressure in said device when calibrated and driven by said control signal as a measure of the instantaneous blood pressure of the subject, wherein calibration of said device comprises the steps of:
   (i) disabling the servo of the device, applying a standing pressure to the fluid in the device, monitoring the instantaneous fluid pressure in said device, and adjusting said standing pressure to a first level at which the monitored fluid pressure provides a first measure of arterial blood pressure at the site of said device;
   (ii) inhibiting arterial blood flow at the site of said pressurisable device, enabling the servo of the device, monitoring the instantaneous fluid pressure in said device, and adjusting the servo gain to a first level at which said first measure of arterial blood pressure is recreated in the fluid of said device, and
   (iii) re-establishing arterial blood flow at the site of said pressurisable device, applying the standing fluid pressure in said device at said first level and applying the servo gain at said first level.

2. The method claimed in claim 1, wherein the step of inhibiting arterial blood flow at the site of said pressurisable device includes obstructing the pertaining artery upstream from said site.

3. The method claimed in claim 1, wherein the step of inhibiting arterial blood flow at the site of said pressurisable device includes adjusting the standing fluid pressure in said device to a level which is in excess of the subject's systolic arterial blood pressure.

4. The method claimed in claim 1, wherein the step of deriving said control signal is effected contemporaneously with the monitoring of the fluid pressure signal in the calibrated device by monitoring the subject's blood pressure at a second site.

5. The method claimed in claim 1, wherein the step of deriving said control signal is effected by temporarily storing preceding waveforms monitored by the fluid pressure signal in the calibrated device.

6. Apparatus for carrying out the method of claim 1, comprising a servo-controlled fluid-pressurisable device adapted to be located in the region of a subject's artery,
   a controllable source of fluid coupled to said device,
   means for monitoring the fluid pressure in the device, means for deriving a control signal from the subject's blood pressure and applying said control signal to the servo of said device,
   means for adjusting the standing pressure of fluid in said device, and
   means for adjusting the gain of the servo of said device.

* * * * *